United States Patent [19]

Van Dellen

[11] 4,248,821

[45] Feb. 3, 1981

[54] METHOD AND DEVICE FOR EMBEDDING A SPECIMEN FOR MICROSCOPIC EXAMINATION

[76] Inventor: Adrian F. Van Dellen, P.O. Box 12502, Department of Pathology Verterinary Research Institute, Onderstepoort, South Africa, 0110

[21] Appl. No.: 60,467

[22] Filed: Jul. 25, 1979

[51] Int. Cl.³ ............................................. A01N 1/00
[52] U.S. Cl. .................................. 264/135; 425/110; 425/126 R; 425/125; 427/4
[58] Field of Search .................. 425/125, 110, 126 R; 427/4; 264/135

[56] References Cited

U.S. PATENT DOCUMENTS

| | | | |
|---|---|---|---|
| 1,793,435 | 2/1931 | Bradley | 425/125 |
| 2,747,230 | 5/1956 | Magnus | 18/59 |
| 2,996,762 | 8/1961 | McCormick | 18/26 |
| 3,130,099 | 4/1964 | Homburger | 156/57 |
| 3,172,149 | 3/1965 | Kornmayer | 425/126 |
| 3,536,911 | 10/1970 | Grasenick et al. | 350/95 |
| 3,558,766 | 1/1971 | Halpert | 264/275 |
| 3,806,577 | 4/1974 | Szebenyi et al. | 264/255 |
| 4,070,495 | 1/1978 | Berger et al. | 427/4 |
| 4,103,041 | 7/1978 | Macho et al. | 427/4 |

*Primary Examiner*—Maurice J. Welsh
*Attorney, Agent, or Firm*—Isaksen, Lathrop, Esch, Hart & Clark

[57] ABSTRACT

A method and device for embedding in a plastic block a selected part of a specimen being prepared for microscopic examination. The device has a frame with a horizontally disposed base member and a vertically disposed headboard and footboard. A mold jockey slides longitudinally along the base member. A slide jocket slides transversely to the direction of motion of the mold jockey and supports a glass microscope slide horizontally above the mold jockey, such that a mold held in the mold jockey may be moved beneath any selected location on the microscope slide. A constricted mouth of a plastic mold held in the mold jockey is pressed against a plastic impregnated specimen held to the underside of the microscope slide. The plastic is cured, embedding a section of the specimen in the face of the plastic block formed within the plastic mold. After curing, excess plastic is removed, leaving the selected portion of the specimen embedded in the end of the plastic block, with a known orientation and location.

9 Claims, 6 Drawing Figures

METHOD AND DEVICE FOR EMBEDDING A SPECIMEN FOR MICROSCOPIC EXAMINATION

BACKGROUND OF THE INVENTION

1. Field of the Invention

This invention relates to electron microscopy and more particularly to equipment for preparing specimens for viewing in an electron microscope.

2. Description of the Prior Art

Before a specimen may be viewed in an electron microscope, it must be processed to remove any water therein and to embed it in a suitable holding medium. Conventionally, the water is removed from a sample of tissue or other material by immersing the specimen in a series of solvent solutions. Each solution contains successively less water than the preceding solution until the final solution is reached, which is water-free. Alternatively, the water in a specimen may be removed by freeze-drying, as described in Grasenick et. al., U.S. Pat. No. 3,536,911. Conventionally, the dehydrated specimen is then placed in a liquid medium capable of polymerization, whereupon the medium is subjected to heat or treated with a catalyst so as to cause it to polymerize into a solid plastic block.

To complete the preparation of the specimen for viewing, it is then necessary to trim the plastic embedding medium to the desired shape and size, to select and isolate that portion of the specimen which the viewer desires to study, and to polish the surface of the plastic to a high degree of smoothness, as is discussed in Szebenyi, et al., U.S. Pat. No. 3,806,577.

These conventional procedures, and other generally related procedures for embedding objects in plastic or other media are described in Magnus, U.S. Pat. No. 2,747,230; McCormick, U.S. Pat. No. 2,996,762; Homeburger, U.S. Pat. No. 3,130,099; Grasenick, et al., U.S. Pat. No. 3,536,911; Halpert, U.S. Pat. No. 3,558,776; and Szebenyi, et al., U.S. Pat. No. 3,806,577.

Specimens for microscopy conventionally are cut into very thin slices by the use of a microtome or similar instrument. These slices are small and fragile, making difficult any attempt to excise a small portion of a slice and embed it in a plastic block in such a manner that the slice remains flat and with a known orientation within the block. The prior art does not disclose convenient means for selecting and isolating a small portion of a specimen prior to embedding or for controlling its configuration and orientation during the embedding process.

SUMMARY OF THE INVENTION

The device of the invention allows a small piece of specimen taken from a slide to be embedded in a small clear plastic block particularly adapted to further processing of the specimen for electron microscope examination. By utilizing the method and device of the invention, it is possible to easily and very accurately select the desired specimen sample and to encapsulate it in a plastic block which requires very little additional processing.

The device of the invention includes a support frame having a headboard and a footboard with a longitudinally disposed base member connected between them. A mold jockey which holds a mold for liquid plastic is mounted to slide longitudinally along the base member between the footboard and headboard. The mold jockey includes a mold pedestal mounted to the base of the mold jockey for upward and downward movement, preferably by rotation of a lifting screw which is rotatably mounted to the mold jockey base and threaded to the mold pedestal. The mold itself is clasped to the top of the mold pedestal and preferably has a small level opening at its top which is filled with the liquid plastic resin in its uncured state. A slide jockey or holder is mounted to the headboard for sliding movement transverse to the direction of movement of the mold jockey. The slide jockey includes a slide clamp which is adapted to firmly hold a specimen slide in a horizontal position above the base member of the frame. The opposite end of the slide is supported in a groove on a slide footrest which extends outwardly from the footboard to engage the end of the slide opposite from that held by the slide jockey. By moving the mold jockey and the slide jockey, the top of the mold held by the mold pedestal can be aligned precisely under a selected area of the specimen on the slide which is to be removed. The mold pedestal is then raised to bring the liquid plastic within the mold into contact with the selected area of the slide.

In the method of the invention, the specimen mounted on the slide is first impregnated with a transparent curable plastic resin in its liquid state. The slide is then mounted on the device of the invention and clamped into the slide jockey with the liquid impregnated specimen side of the slide facing downwardly. Uncured liquid plastic is placed in the top of the mold in the mold pedestal, and the mold is positioned, by movement of the slide jockey and mold jockey, to the desired location under the selected area of the slide. The mold is then elevated by raising the mold pedestal such that the liquid plastic resin in the mold comes into contact with the selected area of the specimen. Conditions are then provided to the slide and the mold so that the liquid plastic resin is cured to a solid state. For example, the liquid resin may be of the heat curing type with curing being obtained by placing the entire device in an oven at a sufficient temperature and for a sufficient period of time to effect the transition of the resin to a solid state. After curing, the mold is separated away from the slide to break the selected area of specimen away from the slide and leave it embedded in the solid plastic block contained within the mold. Generally, the face of the resulting separated plastic block will be quite smooth, since it will have faced the polished glass surface of the slide during curing.

A primary object of the invention is to provide a convenient means for isolating a selected portion of a specimen being prepared for microscopic examination and for embedding the selected portion in a plastic block.

A second object of the invention is to provide a means for excising a selected portion of a flat, thin, and fragile specimen and embedding it in a plastic block without distorting the flatness of the selected portion.

Another object of the invention is to provide a means for embedding a selected portion of a specimen in a plastic block, maintaining the selected portion in a known orientation relative to the rest of the block.

Other objects, features, and advantages of the invention will be apparent from the following detailed description taken in conjunction with the accompanying drawings showing preferred embodiments of a device for embedding in a plastic block a selected part of a specimen being prepared for microscopic examination.

DESCRIPTION OF THE PREFERRED EMBODIMENT

Figure 1:
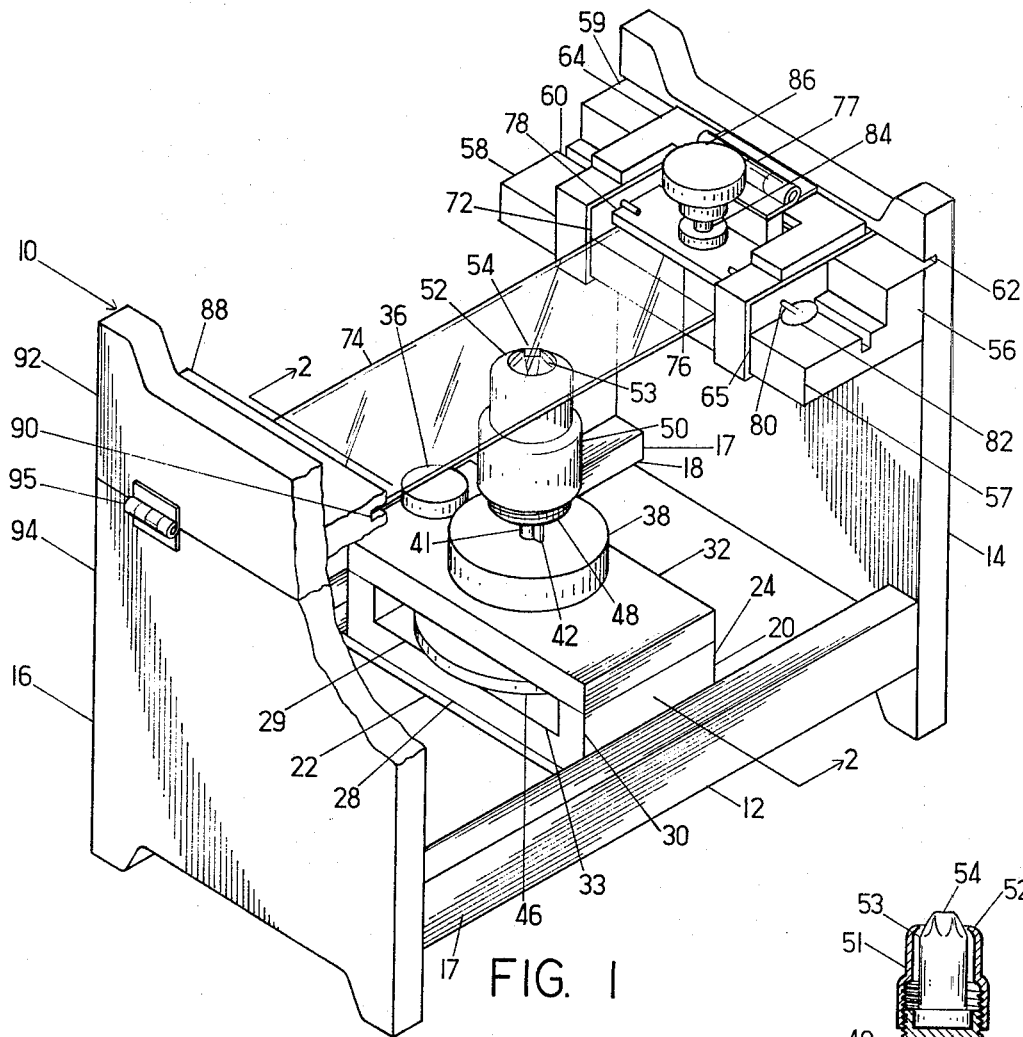
FIG. 1 is a perspective view of the device of my invention, with a portion of the footboard and slide footrest broken away.
Figure 3:
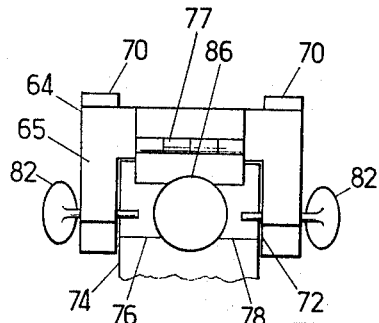
FIG. 3 is a top plan view of the slide jockey.
Figure 2:
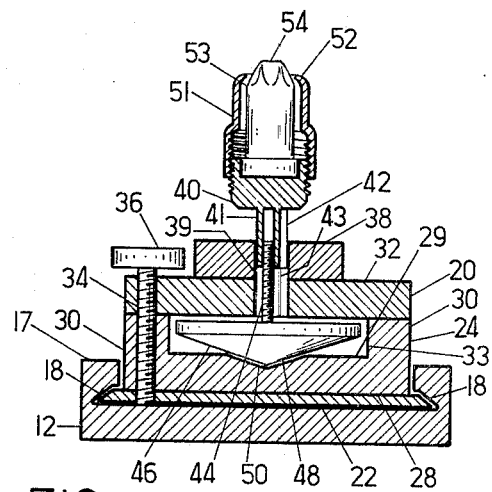
FIG. 2 is a cross-sectional view of the mold jockey and baseboard of my invention, taken along section lines 2—2 of FIG. 1.
Figure 4:
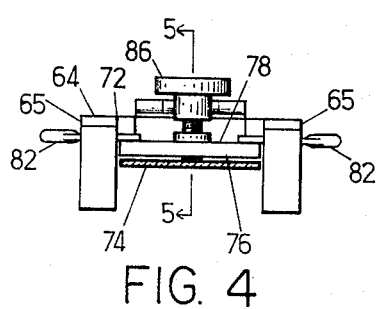
FIG. 4 is a front elevation view of the slide jockey shown in FIG. 3.

Referring more particularly to the drawings, wherein like numbers refer to like parts in each view, FIG. 1 illustrates a preferred embodiment of my novel device for embedding in a plastic block a selected part of a specimen being prepared for microscopic examination, shown generally at 10. The device 10 has a frame which includes a horizontally disposed base member 12. A vertically disposed headboard 14 and vertically disposed footboard 16 are connected rigidly to the base member 12 in opposed relation. The base member 12 has upright longitudinal side boards 17 extending longitudinally between the headboard 14 and footboard 16. The sideboards 17 have grooves 18 formed therein on their inner sides adjacent the bottom of the base member.

A mold jockey 20 has a base 22 adapted to slideably engage the grooves 18 to guide the longitudinal movement of the mold jockey along the base member. The mold jockey base includes a U-shaped bottom member 24 which has a flat bottom panel 28 attached to its bottom surface and which extends outwardly beyond the bottom member to form outwardly extending flanges adapted to engage the walls of the grooves 18. The bottom member 24 has a bottom interior surface 29 and a pair of sidewalls 30. A flat cap member 32 spans the distance between the sidewalls 30 and is attached thereto to form a partially enclosed cavity 33 between the cap member and the interior surfaces of the bottom member.

Internal surfaces within the mold jockey base 22 define a continuous threaded hole 34 extending from the top of the cap 32 to the bottom of the bottom panel 28. A set screw 36 is threadedly engaged in the threaded hole 34 and may be tightened so as to engage the base member 12 beneath the mold jockey, whereby the mold jockey may be releasably secured at a selected position along the length of the grooves 18.

A pedestal support member 38 is rigidly fastened to the top of the cap 32. Internal surfaces in the pedestal support member 38 and the cap member 32 define a continuous opening 39 vertically disposed within the pedestal support member and the cap and extending entirely therethrough. A mold pedestal 40 includes a central tubular shaft 41 selected to have substantially the same cross-sectional size as the opening 39 and which extends downwardly into the opening for a selected distance. A spline 42 extends outwardly from the shaft 41 to engage the walls of a slot 43 in the pedestal support member to prevent rotation of the mold pedestal.

A lifting screw 44 is threadedly engaged in the interior bore of the shaft 41. The lifting screw 44 has a cone shaped head 46 which is substantially contained within the cavity 33 except that the outer edge of the head extends beyond the base to allow the head to be rotated by the fingers of a user. When the lifting screw 44 is rotated, the shaft 41 is moved upwardly or downwardly depending upon the direction of rotation. The cone shaped surface 48 of the head 46 rests in and rotates in a mating cone shaped depression 50 formed in the bottom surface 29 of the bottom member 24.

A mold clasp 51 is mounted to the pedestal 40 and provides a means for securely clasping a plastic mold 53 to the pedestal. The mold 53 seats in a depression formed on the top of the pedestal 40. Internal threads formed in the bore of the clasp 51 engage with external threads formed on the pedestal 40. Installation of a mold is easily accomplished by seating the mold on the pedestal and then screwing the clasp 51 down over the mold until the inwardly extending edges 52 of the clasp engage the tapered top surfaces of the mold. It is apparent that other clasp structures can be utilized and may be required where molds of other shapes are utilized.

The plastic mold 53 is adapted to contain a selected quantity of liquid, uncured plastic of the sort conventionally used to embed specimens for electron microscopy, and is similar to a standard mold known as a beam capsule. However, the mold 53 has a substantially square opening 54 at the tapered end of the mold which is selected to correspond in size with that portion of a larger slice of a specimen which the user wishes to excise and embed in a plastic block, preparatory to examination in a microscope.

A slide headrest 56 is rigidly attached to the headboard 14 and projects toward the footboard 16. The slide headrest 56 has a front surface 57, a substantially horizontal upper surface 58, and an under surface (not shown). The upper surface 58 has a headrest groove 60 extending transversely to the base sideboard grooves 18. The headrest 56 also has a top surface 59 parallel to and spaced above the upper surface 58. A headboard groove 62 extends across the headboard 14 above the slide headrest 56 and substantially parallel to and contiguous with the top surface 59.

Figure 5:
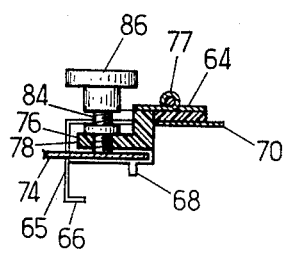
FIG. 5 is a section view of the slide jockey taken along section lines 5—5 of FIG. 4.

A slide jockey 64 having a bracket member 65 is adapted to slide along the slide headrest 56 in a direction parallel to the headrest groove 60. As best shown in FIG. 5, the bracket member 65 has a front slide flange 66, a middle slide key 68 and at least one rear flange 70. The front flange 66 slideably engages the front surface 57 and the under surface of the slide headrest 56. The middle slide key 68 slideably engages the walls of the headrest groove 60, and the rear flange 70 slideably engages the walls of the headboard groove 62, whereby the slide jockey is slideably secured to the headrest 56 and is constrained to slide across the headrest in a direction transverse to that of the base member grooves 18.

The slide jockey 64 has opposed surfaces defining a notch 72 extending vertically through the slide jockey which is sized to receive a laboratory slide. A conventional, glass microscope slide 74 rests on the upper surface 58 of the slide headrest 56 in the notch 72, with the long dimension of the microscope slide 74 extending substantially parallel to the baseboard grooves 18. A slide clamp 76 is attached to the slide jockey bracket 65 by a hinge 77. The slide clamp 76 has a clamp body 78 that extends horizontally over the end of the microscope slide 74 when the slide clamp is in the closed position, as illustrated in FIG. 1. The bracket member 65 has internal surfaces defining at least one and preferably two lock holes 80 extending substantially horizontally through the bracket member. The position of the lock holes 80 is selected to be immediately above the clamp body 78 when the slide clamp 76 is in the closed position. A pin lock 82 extends through each lock hole 80 and over the clamp body 78 when the slide clamp is in the closed position, thereby locking the slide clamp in the closed position.

A slide set screw 84 having a turning head 86 is threaded through the slide clamp 76. When the slide clamp 76 is in the closed position, the slide set screw 84 can be tightened against the glass microscope slide 74, whereby the microscope slide is pressed against the upper surface 58 of the slide headrest 56 and locked in place. With the slide set screw loosened and the pin locks 82 removed, the slide clamp may be rotated upwardly from the slide 74 to allow removal of the slide.

Figure 6:
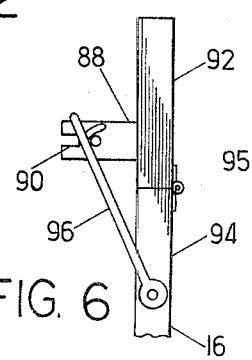
FIG. 6 is a side elevation view of a portion of the footboard.

A slide footrest 88 is rigidly fastened to the footboard 16 in opposed relation to the slide headrest 56. The slide footrest 88 has surfaces defining a footrest groove 90 adapted to receive the end of a microscope slide 74 opposite to that being held in the slide jockey 64, whereby the microscope slide is supported and steadied. The footboard 16 is divided into an upper section 92 and a lower section 94 at a line on the footboard selected to be below the slide footrest 88. The upper section 92 and lower section 94 are fastened together by hinges 95 (one shown) whereby the upper section of the footboard may be swung away from the opposing headboard to facilitate the removal or insertion of a microscope slide 74. The upper section 92 has a closed position, illustrated in FIG. 1, wherein it is substantially in the same plane as the lower section 94, and an open position, wherein it is tipped away from the opposing headboard 14, as described above. A latch 96, shown in FIG. 6 but hidden in FIG. 1, is adapted to rigidly secure the footboard upper section 92 in its closed position.

All parts of the mechanism 10 may be molded or machined from any appropriate, rigid material using conventional techniques. For example, brass, steel, aluminum, or other common metals, or nylon or other moldable or machinable plastics may be used as well as wood and laminates.

When it is desired to embed a specimen in plastic in preparation for a viewing with an appropriate microscope, the user of the device disclosed first obtains a thin slice of the material to be studied, using conventional specimen preparation techniques. The thin slice is placed on a conventional glass microscope slide and is impregnated with transparent uncured plastic resin in its liquid state. The glass slide is then held within the device by the slide jockey 64 and the footrest groove 90, with the specimen on the lower surface of the microscope slide facing downwardly. The surface tension of the liquid plastic is sufficient to prevent the plastic-impregnated sample from dropping off the slide. The mold 53 is filled with the same liquid plastic, suitably prepared for polymerization by the addition of the appropriate catalysts. The mold 53 is filled completely, so that the liquid held within it fills the constricted mouth 54. Because of the high surface tension of the liquid plastic, it is possible to slightly overfill the plastic mold 53, creating a convex meniscus projecting above the constricted mouth 54.

The mouth 54 is centered beneath that part of the thin slice of specimen which has been selected for embedding by manipulation of the mold jockey 20 and the slide jockey 64. The slide set screw 84 is then tightened, locking the microscope slide in place. Similarly, the mold jockey set screw 36 is tightened, securing the mold jockey in place. The head 46 of the lifting screw 44 is then turned, elevating the plastic mold 53 until the constricted mouth 54 is pressed against that part of the thin slice of specimen selected for embedding. The plastic impregnated thin slice of specimen and the plastic contained within the plastic mold join to form a continuous mass of plastic.

After the plastic has cured, either by action of the catalyst or by thermal hardening, the microscope slide 74 is separated away from the plastic mold 53. The molded plastic may be broken away from the microscope glass slide in various ways to lift with it the selected area of specimen which became embedded in the hard plastic within the mold 53. For example, with the latch 96 released, the upper section 92 of the footboard can be rotated backwards and away from the glass slide 74. By providing sufficient tolerance in the groove 90, the rotation of the section 92 will slightly elevate the footboard end of the slide and cause the slide to break free of the hardened plastic in the mold. After the slide footrest has been rotated out of engagement with the slide, the slide set screw 84 can be opened to release the slide and allow it to be pulled horizontally away from the footboard to complete the separation of the slide and the mold. Because the entire slice of specimen was held against the flat surface of the glass microscope slide by the surface tension of the liquid plastic used to impregnate the slice of specimen, the entire slice of specimen, including the small portion selected for embedding, assumed the flat configuration of the surface of the slide. Consequently, the small portion selected for embedding was held flat during the embedding process and has a known location and orientation within the cured plastic block. The surface of the plastic block, molded by the flat surface of the microscope slide, is itself flat and very smooth. Consequently, a minimum of surface preparation is necessary to prepare that surface of the plastic block for ultramicrotomy prior to use in a microscope. The plastic block with the excised portion of specimen can then be further processed for microscopy in a conventional manner.

It is understood that the invention is not confined to the particular construction, materials, and arrangement of parts herein illustrated and described, but embraces all such modified forms thereof as come within the scope of the following claims.

I claim:

1. A device for embedding in a plastic block a selected area of a biological specimen from a specimen slide, comprising:
   (a) a frame, having a vertically disposed headboard and a vertically disposed footboard and a longitudinally disposed base member connected between said headboard and footboard;
   (b) a mold jockey including a base, a mold pedestal mounted to said base for vertical movement with respect to said base, means for raising and lowering said mold pedestal with respect to said base, and mold clasp means mounted on said pedestal for clasping a plastic mold, said mold jockey base being adapted to slidably engage said frame base member for sliding movement therealong between said frame headboard and footboard; and (c) a slide jockey mounted to said headboard for sliding movement transverse to the direction of movement of said mold jockey and including a slide clamp adapted to hold a specimen slide firmly in a horizontal position above said frame base member, whereby the top of a plastic mold held by said mold clasp means may be aligned with a selected location on a specimen slide by moving said mold jockey and said slide jockey until the plastic mold underlies the selected area of the slide, and whereby the plastic mold held by said mold clasp means may be moved up to make contact with the selected location on the slide by said means for raising and lowering said mold pedestal.

2. The device of claim 1 wherein said frame base member includes upright longitudinal sideboards extending between said footboard and headboard and having grooves formed therein on the inner sides of said sideboards, and wherein said mold jockey base has outwardly extending flanges adapted to engage with the walls of said grooves in said frame base member sideboards so as to guide said mold jockey base in sliding longitudinal movement while preventing movement of said mold jockey base in other directions.

3. The device of claim 1 including a slide foot rest extending inwardly from attachment to said footboard and having a groove therein adapted to slidably engage and support the edge of a specimen slide opposite to the edge of the slide held by said slide jockey means.

4. The device of claim 1 wherein said means for raising and lowering said mold pedestal comprises a lifting screw rotatably mounted to said mold jockey base and threadingly attached to said mold pedestal, and wherein said mold pedestal is mounted to said mold jockey base for sliding upward and downward movement without rotation.

5. The device of claim 1 wherein said headboard has a slide headrest member extending from attachment to said headboard, said slide headrest member having a transversly extending groove therein, and wherein said slide jockey is slidably engageable with the walls of said headrest member groove such that said slide jockey is supported by said headrest member and is guided for transverse movement by engagement with the walls of said groove in said headrest member.

6. The device of claim 1 wherein said mold jockey base includes a U-shaped bottom member, a flat cap member which spans the U-shaped bottom member and is attached thereto to form an enclosed cavity between said cap member and the interior surfaces of said U-shaped bottom member, said cap member having a central opening formed therein, a pedestal support member fastened to the top of the cap member and having an opening therein positioned to align with the opening in said cap member and having a slot extending outwardly from the central opening therein, and wherein said mold pedestal has a central tubular shaft adapted to slide upwardly and downwardly in the central opening in said pedestal support member and having a spline extending outwardly therefrom adapted to engage with the walls of said slot in said pedestal support member so as to prevent rotation of said mold pedestal, and wherein said means for raising and lowering said mold pedestal includes a lifting screw threadingly engaged with the interior bore of the tubular shaft of said mold pedestal and having a cone-shaped head affixed to the bottom thereof which is adapted to rest in and rotate in a mating cone-shaped depression formed in the bottom interior surface of said U-shaped bottom member, whereby turning of said cone-shaped head of said lifting screw will cause said mold pedestal to advance upwardly or retract downwardly depending on the direction of rotation of the head of said lifting screw.

7. The device of claim 5 wherein said slide jockey includes a bracket member adapted to rest on and slidably engage said slide headrest member, and wherein said slide clamp is hingedly attached to said slide bracket and adapted to rotate upwardly to allow a slide to be inserted into a position resting a portion of its end on said slide headrest whereupon said slide clamp may be rotated downwardly to clamp firmly against the slide, and further including a locking pin engagable through said bracket member for firmly holding said slide clamp in position clamping the end of a slide held on said slide headrest, and a slide set screw threaded through said slide clamp in position to be turned firmly against a slide held under said slide clamp.

8. The device of claim 1 including a mold held by said mold clasp means, said mold having a top end tapering to a flat edge square opening in which liquid plastic resin may be held.

9. A method of embedding a selected area of a biological specimen from a specimen slide in a plastic block comprising the steps of:

(a) impregnating a specimen mounted on a slide with a transparent curable liquid plastic resin;

(b) mounting the slide with impregnated specimen side facing downwardly;

(c) providing a quantity of the liquid plastic resin in a mold positioned beneath a selected area of the specimen on the slide with the liquid plastic resin filling the mold at least to its top edges;

(d) elevating the mold to the slide such that liquid plastic resin in the mold is in contact with the selected area of the specimen;

(e) curing the liquid plastic resin in the mold and on the slide to a substantially solid state; and (f) after curing, separating the mold away from the slide to break the selected area of specimen away from the slide and thereby leave it embedded in the solid plastic block contained within the mold.

* * * * *